US010173980B2

(12) United States Patent
Zhang

(10) Patent No.: US 10,173,980 B2
(45) Date of Patent: Jan. 8, 2019

(54) MIXED DISULFIDE CONJUGATES OF THIENOPYRIDINE COMPOUNDS AND USES THEREOF

(71) Applicant: The Regents of the University of Michigan, Ann Arbor, MI (US)

(72) Inventor: Haoming Zhang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/570,115

(22) PCT Filed: Apr. 29, 2016

(86) PCT No.: PCT/US2016/030261
§ 371 (c)(1),
(2) Date: Oct. 27, 2017

(87) PCT Pub. No.: WO2016/176644
PCT Pub. Date: Nov. 3, 2016

(65) Prior Publication Data
US 2018/0155289 A1 Jun. 7, 2018

Related U.S. Application Data

(60) Provisional application No. 62/155,231, filed on Apr. 30, 2015.

(51) Int. Cl.
| | |
|---|---|
| *C07D 211/72* | (2006.01) |
| *A61K 45/06* | (2006.01) |
| *A61K 47/52* | (2017.01) |
| *A61P 9/00* | (2006.01) |
| *A61K 9/00* | (2006.01) |
| *A61K 31/445* | (2006.01) |
| *A61K 31/4525* | (2006.01) |
| *A61K 31/4535* | (2006.01) |
| *A61K 31/454* | (2006.01) |
| *A61K 31/4545* | (2006.01) |
| *A61K 31/506* | (2006.01) |
| *A61K 31/53* | (2006.01) |
| *A61K 31/5395* | (2006.01) |
| *A61K 31/541* | (2006.01) |
| *C07D 401/06* | (2006.01) |
| *C07D 405/06* | (2006.01) |
| *C07D 409/06* | (2006.01) |
| *C07D 413/06* | (2006.01) |
| *C07D 417/06* | (2006.01) |
| *C07D 419/06* | (2006.01) |
| *C07D 401/12* | (2006.01) |
| *C07D 405/12* | (2006.01) |
| *C07D 409/12* | (2006.01) |
| *C07D 413/12* | (2006.01) |
| *C07D 417/12* | (2006.01) |
| *C07D 419/12* | (2006.01) |

(52) U.S. Cl.
CPC .......... *C07D 211/72* (2013.01); *A61K 9/0019* (2013.01); *A61K 31/445* (2013.01); *A61K 31/454* (2013.01); *A61K 31/4525* (2013.01); *A61K 31/4535* (2013.01); *A61K 31/4545* (2013.01); *A61K 31/506* (2013.01); *A61K 31/53* (2013.01); *A61K 31/5395* (2013.01); *A61K 31/541* (2013.01); *A61K 45/06* (2013.01); *A61K 47/52* (2017.08); *A61P 9/00* (2018.01); *C07D 401/06* (2013.01); *C07D 401/12* (2013.01); *C07D 405/06* (2013.01); *C07D 405/12* (2013.01); *C07D 409/06* (2013.01); *C07D 409/12* (2013.01); *C07D 413/06* (2013.01); *C07D 413/12* (2013.01); *C07D 417/06* (2013.01); *C07D 417/12* (2013.01); *C07D 419/06* (2013.01); *C07D 419/12* (2013.01); *C07B 2200/07* (2013.01); *C07B 2200/09* (2013.01)

(58) Field of Classification Search
CPC .................................................... C07D 211/72
See application file for complete search history.

(56) References Cited

U.S. PATENT DOCUMENTS 6,610,708 B1 8/2003 Asai et al.

FOREIGN PATENT DOCUMENTS

| WO | 2007/124472 | 3/2007 |
| WO | 2014/109987 | 7/2014 |

OTHER PUBLICATIONS

Algaier I, et al., "Interaction of the active metabolite of prasugrel, R-138727, with cysteine 97 and cysteine 175 of the human P2Y12 receptor" (2008) J Thromb Haemost 6(11):1908-1914.
Bouman HJ, et al., "Paraoxonase-1 is a major determinant of clopidogrel efficacy." (2011) Nat Med 17(1):110-116.
Dansette, PM, et al. "Metabolic oxidative cleavage of thioesters: evidence for the formation of sulfenic acid intermediates in the bioactivation of the antithrombotic prodrugs ticlopidine and clopidogrel." (2009) Chem Res Toxicol 22(2)369-373.
Dansette, PM, et al. "Cytochromes P450 catalyze both steps of the major pathway of clopidogrel bioactivation, whereas paraoxonase catalyzes the formation of a minor thiol metabolite isomer." (2012) Chem Res Toxicol 25(2):348-356.
Dansette, PM, et al. "Metabolic Activation of Prasugrel: Nature of the Two Competitive Pathways Resulting in the Opening of Its Thiophene Ring" (2012) Chem Res Toxicol 25(5):1058-1065.
Dansette PM, et al. "Formation and Fate of a Sulfenic Acid Intermediate in the Metabolic Activation of the Antithrombotic Prodrug Prasugrel†" (2010) Chem Res Toxicol 23(7)1268-1274.

(Continued)

*Primary Examiner* — Bruck Kifle
(74) *Attorney, Agent, or Firm* — Casimir Jones, SC; Robert A. Goetz

(57) ABSTRACT

This invention is in the field of medicinal chemistry. In particular, the invention relates to mixed disulfide conjugates of thienopyridine compounds, and their use as therapeutics for the treatment, amelioration, and prevention of cardiovascular diseases.

9 Claims, No Drawings

(56) References Cited

OTHER PUBLICATIONS

Dick, RJ, et al. "Clopidogrel Resistance: case reports of CYP2C19 gene variants in suspected coronary stent thrombosis." (2011) Heart Lung Circ 20(10):657-658.
Ding Z, et al., "Inactivation of the human P2Y12 receptor by thiol reagents requires interaction with both extracellular cysteine residues, Cys17 and Cys270" (2003) Blood 101(10):3908-3914.
Farid et al. "Metabolism and Disposition of the Thienopyridine Antiplatelet Drugs Ticlopidine, Clopidogrel, and Prasugrel in Humans" The Journal of Clinical Pharmacology, Mar. 2013, vol. 50, p. 126-142.
Freedman and Hylek "Clopidogrel, genetics, and drug responsiveness." (2009) New Engl J Med 360(4):411-413.
Gurbel PA and Tantry US "Clopidogrel resistance?" (2007) Thromb Res 120(3):311-321.
International Search Report and Written Opinion, International Application No. PCT/US2016/030261, dated Aug. 5, 2016.
Kazui M, et al., "Identification of the human cytochrome P450 enzymes involved in the two oxidative steps in the bioactivation of clopidogrel to its pharmacologically active metabolite." (2010) Drug Metab Dispos 38(1):92-99.
Laizure et al. "The Role of Human Carboxylesterases in Drug Metabolism: Have We Overlooked Their Importance?" Pharmacotherapy, Feb. 2013, vol. 33, p. 210-222.
Mason, PJ et al. "Aspirin resistance and atherothrombotic disease." (2005) J Am Coll Cardiol 46(6):986-993.
Savi P, et al., "Identification and biological activity of the active metabolite of clopidogrel." (2000) Thromb Haemost 84(5):891-896.
Sofi F, et al., "Cytochrome P450 2C19*2 polymorphism and cardiovascular recurrences in patients taking clopidogrel: a meta-analysis." (2011) Pharmacogenomics J 11(3):199-206.
Zhang et al. "Formation of the Thiol Conjugates and Active Metabolite of Clopidogrel by Human Liver Microsomes" (2012) Mol Pharmacol 82:302-309.
Supplementary European Search Report, EP Patent Application No. 16787274.6, dated Aug. 16, 2018, six pages.
Zhang et al. "Formation, Reactivity and Antiplatelet Activity of Mixed Disulfide Conjugates of Clopidogrel" Molecular Pharmacology, vol. 83, Apr. 1, 2013, pp. 848-856.

MIXED DISULFIDE CONJUGATES OF THIENOPYRIDINE COMPOUNDS AND USES THEREOF

CROSS-REFERENCE TO RELATED APPLICATIONS

The present application is a national stage of International (PCT) Patent Application Serial No. PCT/US2016/030261, filed Apr. 29, 2016, which claims priority to U.S. Provisional Patent Application No. 62/155,231, filed Apr. 30, 2015, which are hereby incorporated by reference in their entireties.

FIELD OF THE INVENTION

This invention is in the field of medicinal chemistry. In particular, the invention relates to mixed disulfide conjugates of thienopyridine compounds, and their use as therapeutics for the treatment, amelioration, and prevention of cardiovascular diseases.

INTRODUCTION

Thienopyridinyl compounds are widely used as antiplatelet agents to prevent heart attack and stroke. In this category, clopidogrel (Plavix), ticlopidine (Ticlid) and prasugrel (Effient) are three commonly used prodrugs. These agents require polymorphic cytochrome (P450) mediated oxidative bioactivation. Such oxidative bioactivation results in slow on-set of therapeutic effect and several adverse effects including neutropenia and thrombotic thrombocytopenic purpura.

Improved antiplatelet agents not requiring polymorphic cytochrome (P450) mediated oxidative bioactivation are needed.

SUMMARY OF THE INVENTION

Clopidogrel (Plavix), ticlopidine (Ticlid) and prasugrel (Effient) belong to a class of thienopyridinyl compounds widely used as antiplatelet agents to prevent heart attack and stroke. However, several serious drawbacks have been associated with these drugs including lack of response, toxicity and excessive bleeding. These drawbacks are closely related to the fact that they are all prodrugs that require oxidative bioactivation by polymorphic cytochromes P450 enzymes (P450s).

To overcome drawbacks associated with thienopyridine compounds (Clopidogrel (Plavix), ticlopidine (Ticlid) and prasugrel (Effient)), the present invention provides mixed disulfide conjugates of thienopyridine compounds. It is contemplated that such mixed disulfide conjugates of thienopyridine compounds of the present invention are capable of producing active thienopyridine metabolites (e.g., active thienopyridine metabolites capable of antiplatelet activity) in the presence of endogenous glutathione (GSH) without the need for bioactivation by P450s. This approach not only bypasses the oxidative bioactivation process by P450s, but circumvents many of the drawbacks associated with thienopyridinyl drugs. For example, it is contemplated that the mixed disulfide conjugates of thienopyridine compounds of the present invention improve dosing consistency because production of the active metabolite from the conjugates is predictable. In addition, it is contemplated that use of the mixed disulfide conjugates of thienopyridine compounds of the present invention as antiplatelet agents reduce the toxicity as toxic reactive metabolites will not be produced by the thiol-exchange reaction. In addition, the therapeutic onset time for the mixed disulfide conjugates of thienopyridine compounds of the present invention is shortened, which greatly benefits patients who experience acute cardiovascular events. For example, the standard regimen for thienopyridines requires continuously dosing patients for 3-5 days as only a small percentage of ingested thienopyridines are converted to the active metabolite. In contrast, it is contemplated that the mixed disulfide conjugates of thienopyridine compounds of the present invention will release the active metabolites with high yields in less than 5 min. In addition, it is contemplated that the mixed disulfide conjugates of thienopyridine compounds of the present invention will have superior stability over the active metabolites and therefore can be used to quantitatively generate the active metabolites for basic and clinical research in vitro.

Accordingly, in certain embodiments, the present invention provides mixed disulfide conjugates of thienopyridine compounds capable of overcoming such drawbacks associated with thienopyridinyl compounds widely used as antiplatelet agents (e.g., Clopidogrel (Plavix), ticlopidine (Ticlid) and prasugrel (Effient)).

The present invention is not limited to particular mixed disulfide conjugates of thienopyridine compounds. In some embodiments, the mixed disulfide conjugates of thienopyridine compounds are described by Formula I:

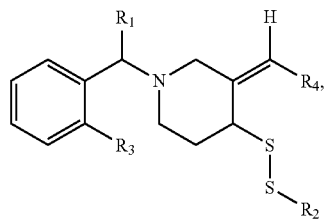

including pharmaceutically acceptable salts, solvates, and/or prodrugs thereof, wherein R4 is selected from the group consisting of an ester moiety with an aliphatic and/or aromatic substituent, a ketone moiety with an aliphatic and/or aromatic substituent, and an amide moiety with an aliphatic and/or aromatic substituent.

Formula I is not limited to a particular chemical moiety R1, R2, R3, and R4. In some embodiments, R1, R2, R3, and R4 each independently include any chemical moiety that renders the resulting compound capable of producing active thienopyridine metabolites upon interaction with endogenous glutathione (GSH) (e.g., active thienopyridine metabolites capable of antiplatelet activity). In some embodiments R1, R2, R3, and R4 each independently include any chemical moiety that renders the resulting compound capable of producing active thienopyridine metabolites in the presence of endogenous glutathione (GSH) without the need for bioactivation by P450s. In some embodiments, R1, R2, R3, and R4 each independently include any chemical moiety that renders the resulting compound capable of treating, ameliorating, or preventing cardiovascular disorders (e.g., coronary artery disease, peripheral vascular disease, and cerebrovascular disease) in a patient, such as those that are responsive to antiplatelet agents (such as clopidogrel, ticlopidine, and prasugrel). In some embodiments, R1, R2, R3, and R4 each independently include any chemical moiety that renders the resulting compound capable of inhibiting platelet aggregation by, for example, altering the function of platelet membranes by blocking ADP receptors (e.g., thereby preventing a conformational change of glycoprotein IIb/IIIa which allows platelet binding to fibrinogen). In some embodiments, R1, R2, R3, and R4 each independently include any chemical moiety that renders the resulting compound capable of reducing aggregation ("clumping") of platelets by irreversibly binding to $P2Y_{12}$ receptors.

Such mixed disulfide conjugates are not limited to particular stereochemical configurations within Formula I

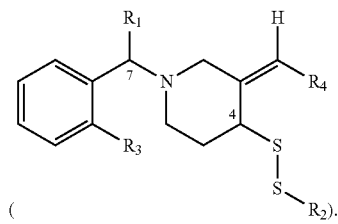

In some embodiments, the double bond connected with the R4 substituent is either in a Z or cis configuration. For example, in some embodiments, Formula I is represented by any of the following stereochemical configurations:

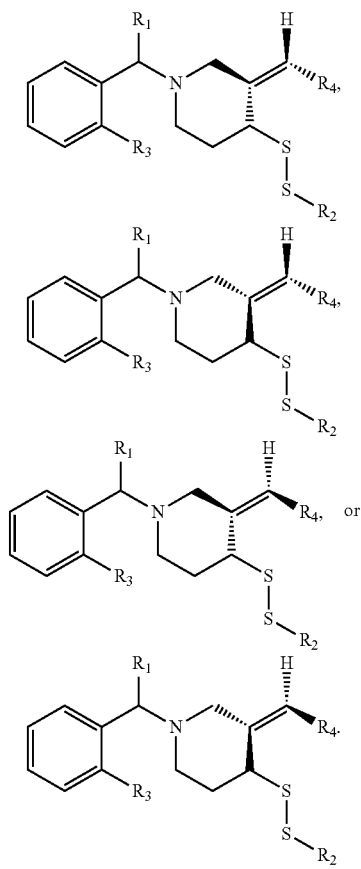

In some embodiments, the C7 carbon is either in a racemic, R or S configuration. For example, in some embodiments, Formula I is represented by any of the following stereochemical configurations:

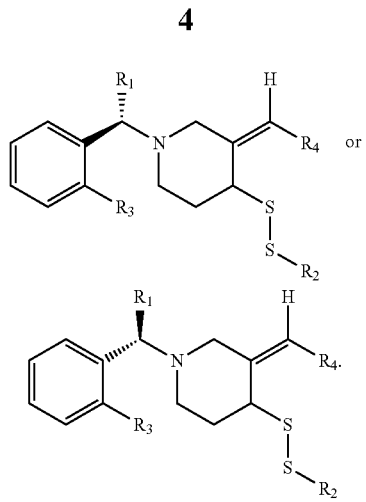

In some embodiments, the C7 carbon is either in a racemic, R or S configuration. For example, in some embodiments, Formula I is represented by any of the following stereochemical configurations:

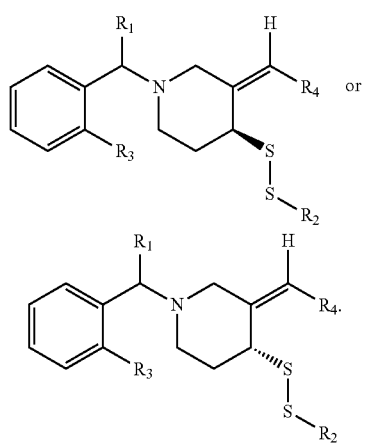

In some embodiments, the compound encompassed within Formula I contains one or more stereochemical configurations for the double bond connected to R4 (e.g., Z or cis configuration), the C7 carbon (e.g., racemic, R or S configuration), and the C4 carbon (e.g., racemic, R or S configuration).

In some embodiments, the compound encompassed within Formula I is in a pharmaceutically acceptable salt form. For example, in some embodiments, the R4 substituent is engaged with an applicable metal to form a salt (e.g., Li, Na, K, etc)

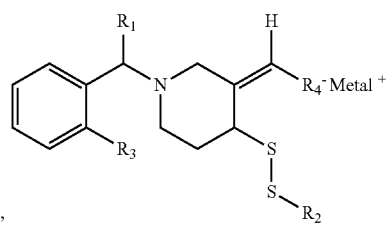

For example, in some embodiments, the R4 substituent has therein a Nitrogen moiety having a positive charge

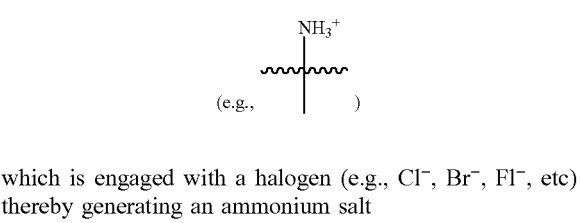
which is engaged with a halogen (e.g., Cl⁻, Br⁻, Fl⁻, etc) thereby generating an ammonium salt
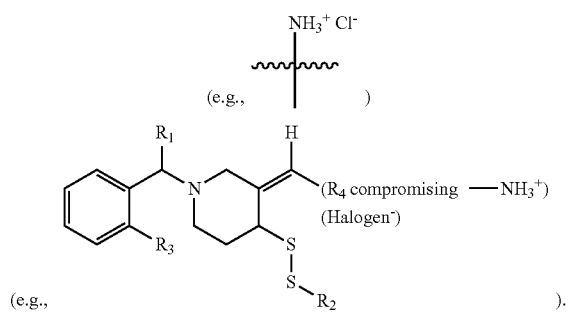
In some embodiment, R1 is selected from the group consisting of H, —CO—OCH3,
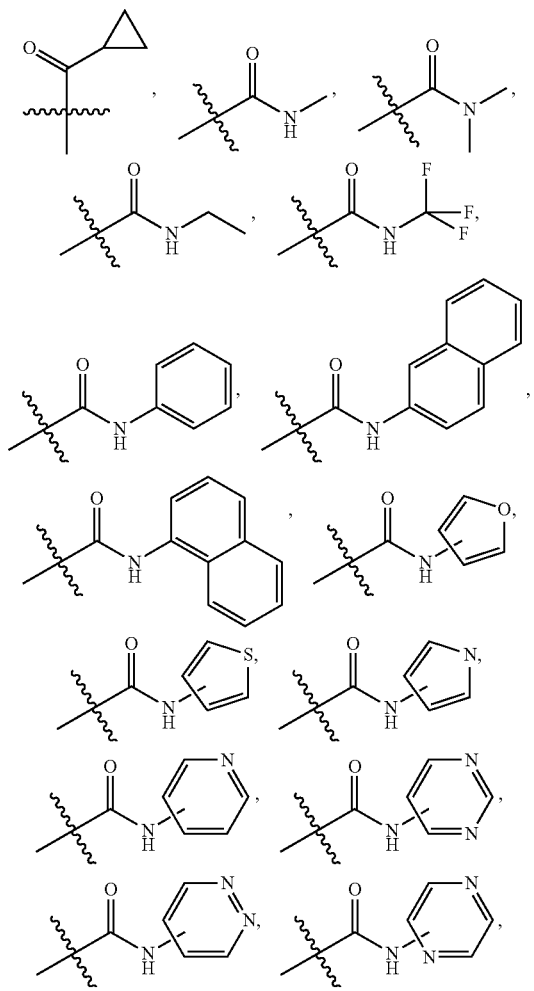
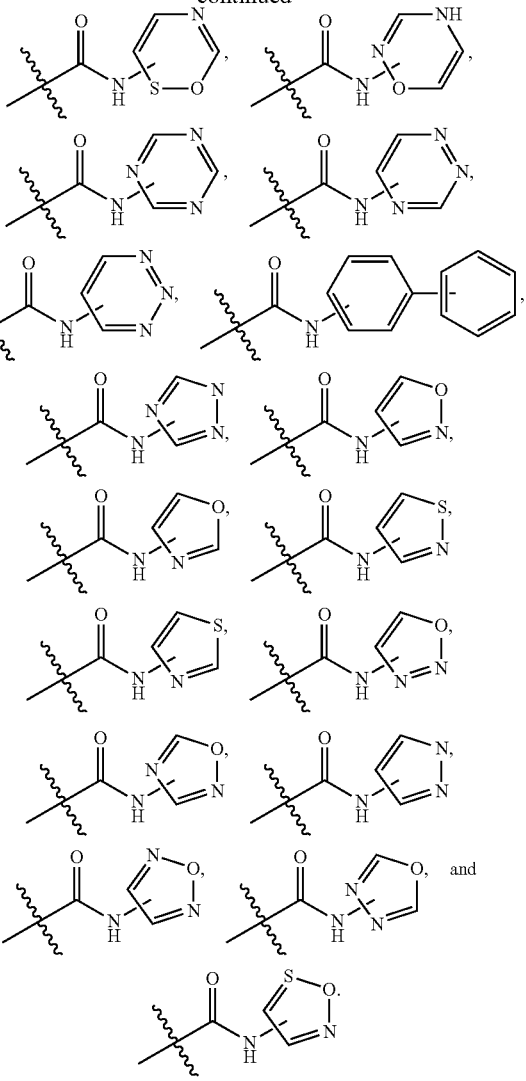
In some embodiments, R2 is selected from the group consisting of
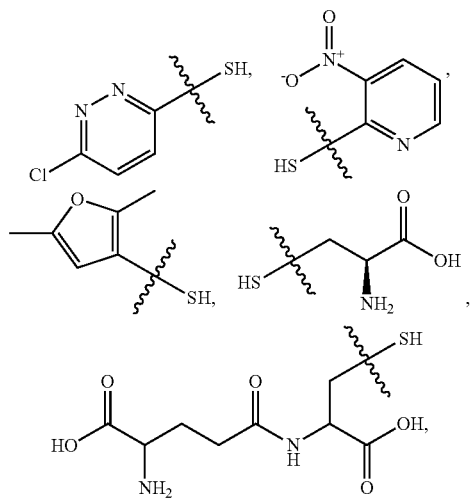

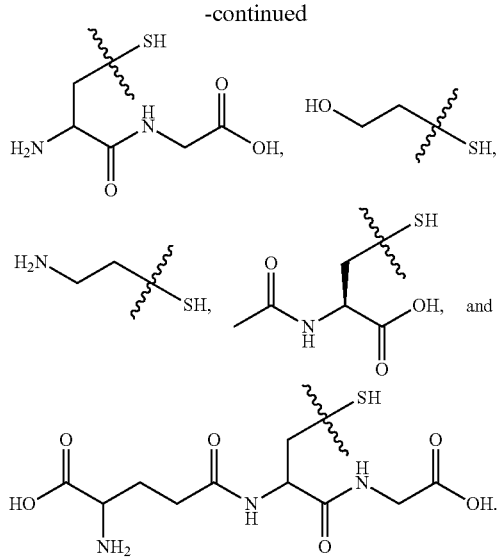

In some embodiments, R3 is an electron withdrawing group. In some embodiments, R3 is a halogen. In some embodiments, R3 is selected from Cl, Br, I, F, CN, NO$_2$, CF$_3$, H, OCH$_3$. In some embodiments, R3 is selected from a halogenated hydrocarbon group such as a trifluoromethyl group; a carboxyl group; an alkoxycarbonyl group such as a methoxycarbonyl group; an aryloxycarbonyl group such as a phenoxycarbonyl group; abn acyl group such as an acetyl group; an acyloxy groups such as an acetoxy group; a cyano group; an aryl group; a 1-alkenyl group; a nitro group; a sulfo group; an alkanesulfonyl group; an alkanesulfinyl group; and an alkoxysulfonyl group.

In some embodiments, R4 is any form of a salt.

In some embodiments, R4 is selected from —COOCH3, —COOCH2CH3, COOCF3,

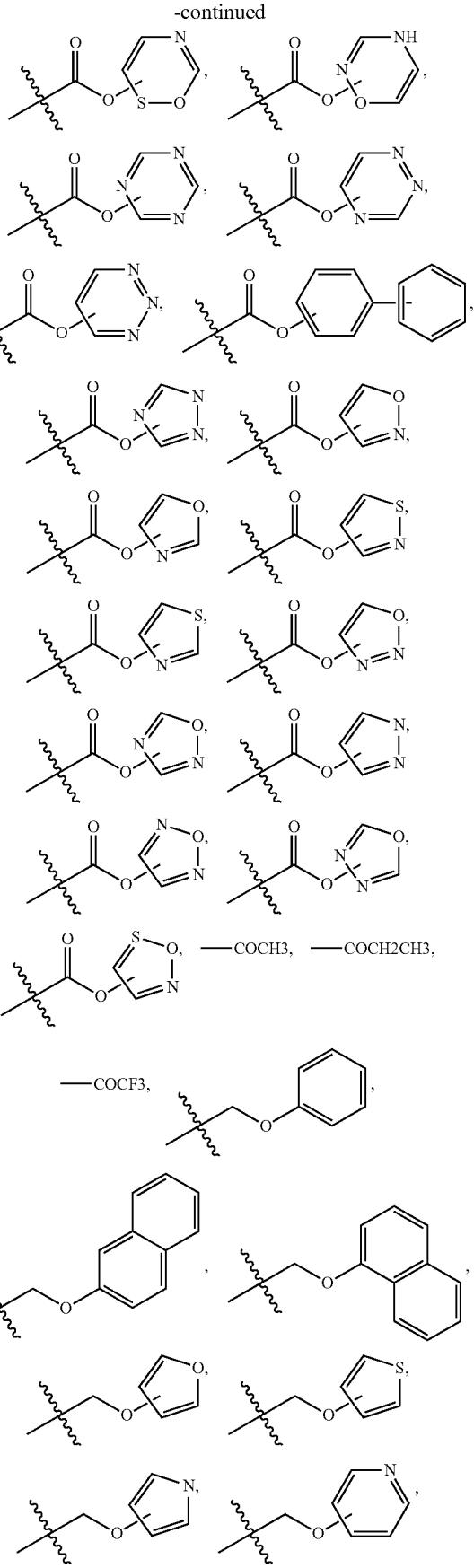

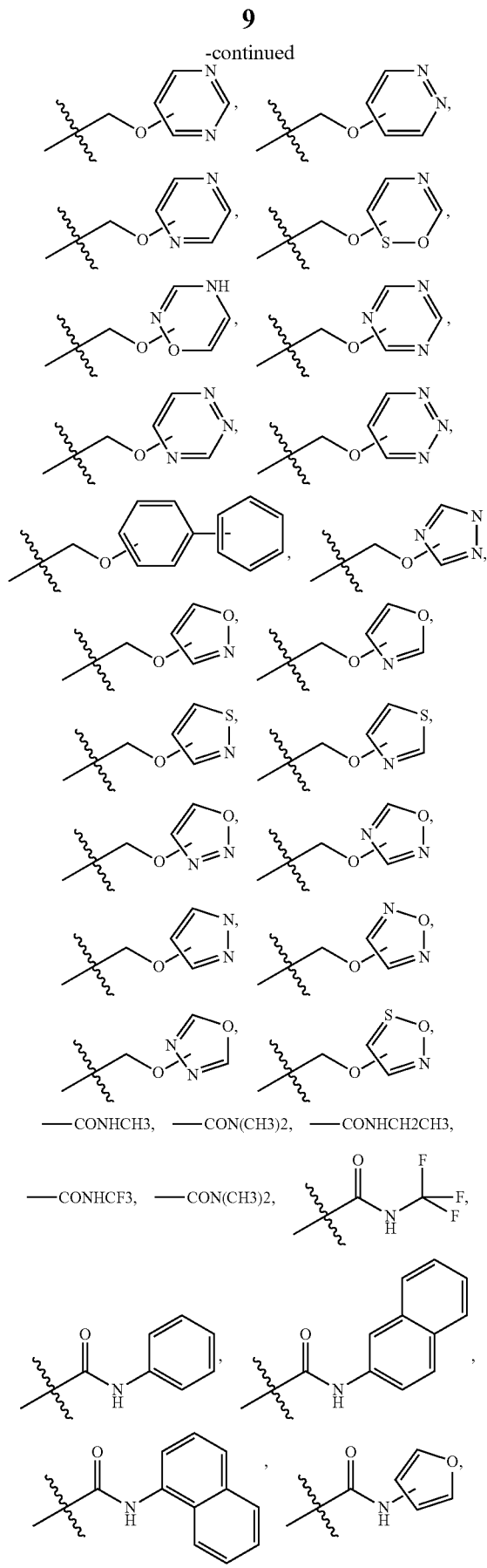
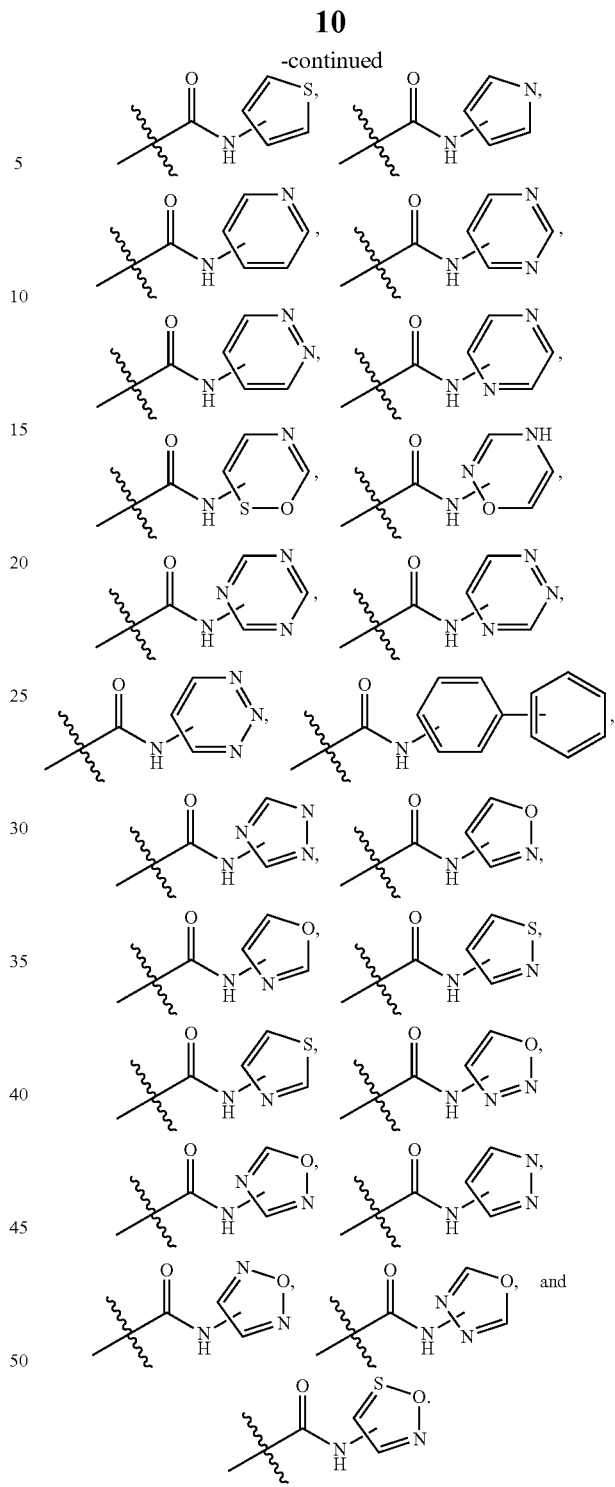

In some embodiments, the compounds encompassed within Formula I are stable in isolated form.

In some embodiments, the compounds are conjugated with a targeting moiety. For example, in some embodiments, the compounds are conjugated with an agent for targeting tumor cells. In some embodiments, the compounds are conjugated with antibodies that target tumor cells.

In certain embodiments, the present invention provides pharmaceutical compositions comprising a mixed disulfide conjugate of a thienopyridine compound and a pharmaceutically acceptable carrier.

In certain embodiments, the present invention provides pharmaceutical compositions comprising mixed disulfide conjugates of thienopyridine compounds configured for intravenous (IV) administration. In some embodiments, such pharmaceutical compositions comprising mixed disulfide conjugates of thienopyridine compounds configured for intravenous (IV) administration are used in the treatment, amelioration and prevention of atherothrombosis. In some embodiments, such pharmaceutical compositions comprising mixed disulfide conjugates of thienopyridine compounds configured for intravenous (IV) administration are used for rapid inhibition of platelet aggregation. In some embodiments, such pharmaceutical compositions comprising mixed disulfide conjugates of thienopyridine compounds configured for intravenous (IV) administration are used during percutaneous coronary intervention procedures (e.g., coronary angioplasty) for rapid inhibition of platelet aggregation.

In certain embodiments, the present invention provides methods of treating, ameliorating, or preventing a cardiovascular disease comprising administering to a patient a therapeutically effective amount of a mixed disulfide conjugate of a thienopyridine compound. In some embodiments, the administration is intravenous administration. In some embodiments, the cardiovascular disease is selected from the group consisting of coronary artery disease, peripheral vascular disease, and cerebrovascular disease. In some embodiments, the compound reduces aggregation of platelets (e.g., through irreversible binding to $P2Y_{12}$ receptors) (e.g., through blocking ADP receptors). In some embodiments, the compound is capable of producing active thienopyridine metabolites in the presence of endogenous glutathione without the need for bioactivation by P450s. In some embodiments, the methods further comprise co-administration of at least one agent selected from the group consisting of a HMG-CoA reductase inhibitor, an ACE Inhibitor, a Calcium Channel Blocker, a Platelet Aggregation Inhibitor, a Polyunsaturated Fatty Acid, Fibric Acid Derivative, a Bile Acid Sequestrant, an Antioxidant, and an Antianginal Agent.

In certain embodiments, the present invention provides methods of treating, ameliorating, or preventing aggregation of platelets onto blood vessels in a patient, comprising administering to the patient a therapeutically effective amount of a mixed disulfide conjugate of a thienopyridine compound. In some embodiments, the administration is intravenous administration. In some embodiments, the patient has or is at risk for developing cardiovascular disease (e.g., coronary artery disease, peripheral vascular disease, and cerebrovascular disease). In some embodiments, the treating, ameliorating, or preventing the aggregation of the platelets occurs through irreversible binding to $P2Y_{12}$ receptors. In some embodiments, the treating, ameliorating, or preventing the aggregation of the platelets occurs through blocking ADP receptors. In some embodiments, the mixed disulfide conjugate of thienopyridine compound is capable of producing active thienopyridine metabolites in the presence of endogenous glutathione without the need for bioactivation by P450s.

Definitions

The term "thienopyridine compound" as used herein, refers to a class of ADP receptor/P2Y12 inhibitors used for their anti-platelet activity. Examples include, but are not limited to, clopidogrel (Plavix), ticlopidine (Ticlid), and Prasugrel (Effient).

The term "mixed disulfide conjugate of a thienopyridine compound" as used herein, refers to a modified thienopyridine compound capable of producing active thienopyridine metabolites upon interaction with endogenous glutathione (GSH).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment and/or prevention of platelet aggregation onto a blood vessel, in one embodiment, a therapeutically effective amount will refer to the amount of a therapeutic agent (e.g., a mixed disulfide conjugate of a thienopyridine compound) that decreases the reduces and/or prevents platelet aggregation by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Thienopyridinyl antiplatelet agents include three clinically used drugs, clopidogrel (Plavix), ticlopidine (Ticlid), and prasugrel (Effient). Their chemical structures and IUPAC names for clopidogrel (Plavix), ticlopidine (Ticlid), and prasugrel (Effient) are as follows:

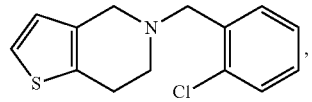

(ticlopidine; 5-(2-chlorobenzyl)-4,5,6,7-tetrahydrothieno[3,2c]pyridine)

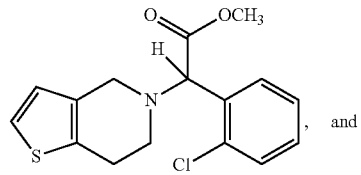

(clopidogrel; (+)-(S)-methyl 2-(2-chlorophenyl)-2-(6,7-dihdrothieno[3,2-c]pyridine-5(4H)-yl)acetate)

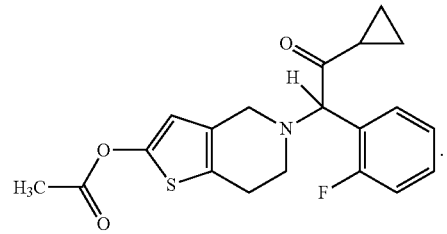

(prasugrel; (RS)-5-[2-cyclopropyl-1-(2-fluorophenyl)-2-oxoethyl]-4,5,6,7-tetrahydrothieno[3,2-c]pyridine-2-yl)acetate)

Thienopyridinyl antiplatelet agents are widely used to treat patients with acute cardiovascular syndromes and peripheral vascular diseases, particularly among those undergoing percutaneous coronary intervention (e.g., coronary angioplasty) to prevent heart attack and stroke. Nearly two million patients receive coronary and carotid stents every year in the United States and the annual sales for Plavix alone was worth $6.5 billion in 2010.

In spite of widespread use, clopidogrel has shown significant inter-individual variability in its efficacy (see, e.g., Freedman J E and Hylek E M (2009) New Engl J Med 360(4):411-413; Gurbel P A and Tantry U S (2007) Thromb Res 120(3):311-321; Sofi F, et al., (2011) Pharmacogenomics J 11(3):199-206). Nearly one-third of patients do not respond to clopidogrel therapy (see, e.g., Mason P J, Jacobs A K and Freedman J E (2005) J Am Coll Cardiol 46(6): 986-993). A large number of studies have been carried out attempting to identify genetic markers that correlate with the lack of response with the aim of overcoming this inter-individual variability. It has been shown that clopidogrel is less effective in patients who carry the mutant CYP2C19*2 gene (see, e.g., Dick R J, Dear A E and Byron K A (2011) Heart Lung Circ 20(10):657-658; Shuldiner A R, et al., (2009) JAMA 302(8):849-857; Sofi F, et al., (2011) Pharmacogenomics J 11(3):199-206). However the CYP2C19*2 mutant gene accounts for only 12% of the variations in response (see, e.g., Shuldiner A R, et al., (2009) JAMA 302(8):849-857). Other factors are likely involved, but have not been identified.

Indeed, though widely used as antiplatelet agents, there are drawbacks associated with thienopyridinyl antiplatelet agents. A major shortcoming for clopidogrel is a dosing inconsistency. For example, nearly one-third of patients do not respond to clopidogrel treatment. Ticlopidine can cause a series of adverse effects ranging from moderate symptoms of skin rashes and diarrhea to severe and sometimes fatal ones such as neutropenia and bone marrow aplasia. In rare cases it causes severe idiosyncratic events of agranulocytosis. Excessive bleeding has been associated with the use of prasugrel, particularly in older patients.

Such drawbacks associated with thienopyridinyl antiplatelet agents are closely related to the fact that these three drugs are all prodrugs that require oxidative bioactivation to the active metabolite (AM) by polymorphic cytochromes P450 (P450s) as illustrated in Scheme 1. Because of this oxidative bioactivation process, the amount of the active metabolite produced by P450s varies with the genetic makeup of each patient's hepatic P450s. Furthermore, these drugs are extensively metabolized by P450s to produce multiple metabolites, some of which are highly reactive and potentially toxic. It has been reported that the severe idiosyncratic events due to ticlopidine are associated with the production of reactive metabolites.

As noted, the variable response to clopidogrel therapy is closely related to the fact that clopidogrel is a prodrug that requires oxidative bioactivation by cytochromes P450 (P450s) to its pharmacologically active metabolite (AM) (see, e.g., Kazui M, et al., (2010) Drug Metab Dispos 38(1):92-99; Savi P, et al., (2000) Thromb Haemost 84(5): 891-896). It is well documented that P450-mediated bioactivation involves two consecutive oxidative steps (see, e.g., Dansette P M, Thebault S, Bertho G and Mansuy D (2010) Chem Res Toxicol 23(7):1268-1274; Dansette P M, Rosi J, Bertho G and Mansuy D (2012) Chem Res Toxicol 25(2): 348-356); clopidogrel is first monoxygenated to 2-oxoclopidogrel, which is in turn oxidized to the AM in the second step. Although it has been argued that esterase PON1 is responsible for converting 2-oxoclopidogrel to the AM (see, e.g., Bouman H J, et al., (2011) Nat Med 17(1):110-116), increasing evidence supports the idea that 2-oxoclopidogrel is converted to the AM via a sulfenic acid intermediate (see, e.g., Dansette P M, Libraire J, Bertho G and Mansuy D (2009) Chem Res Toxicol 22(2):369-373; Dansette P M, Rosi J, Bertho G and Mansuy D (2012) Chem Res Toxicol 25(2):348-356; Dansette P M, Rosi J, Debernardi J, Bertho G and Mansuy D (2012) Chem Res Toxicol 25(5):1058-

Scheme 1.

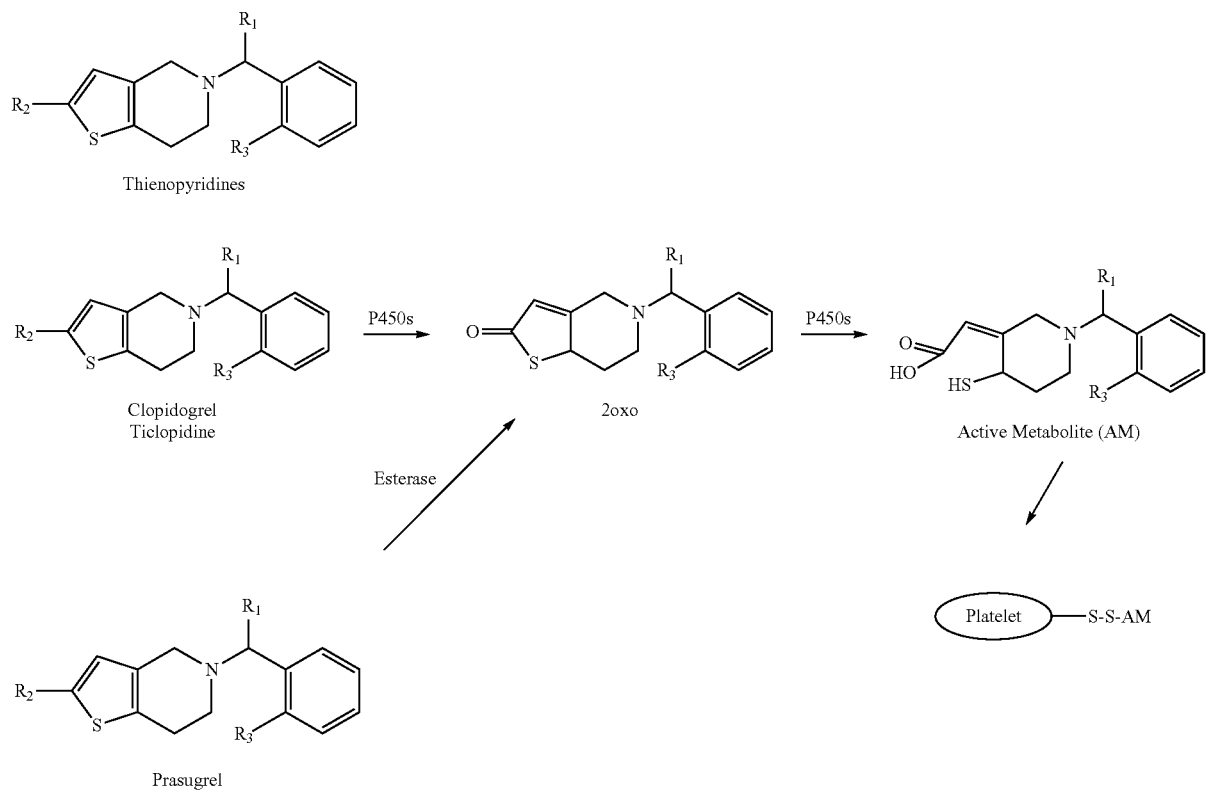

Ticlopidine, R1 = H, R2 = H, R3 = Cl
Clopidogrel, R1 = -CO-OCH3, R2 = H, R3= Cl

Prasugrel, R1 = 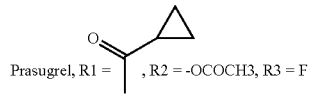, R2 = -OCOCH3, R3 = F

1065; Dansette P M, Thebault S, Bertho G and Mansuy D (2010) Chem Res Toxicol 23(7):1268-1274), as illustrated in Scheme 2.

the mixed disulfide conjugates of thienopyridine compounds of the present invention will improve dosing consistency because production of the active metabolite from the con-

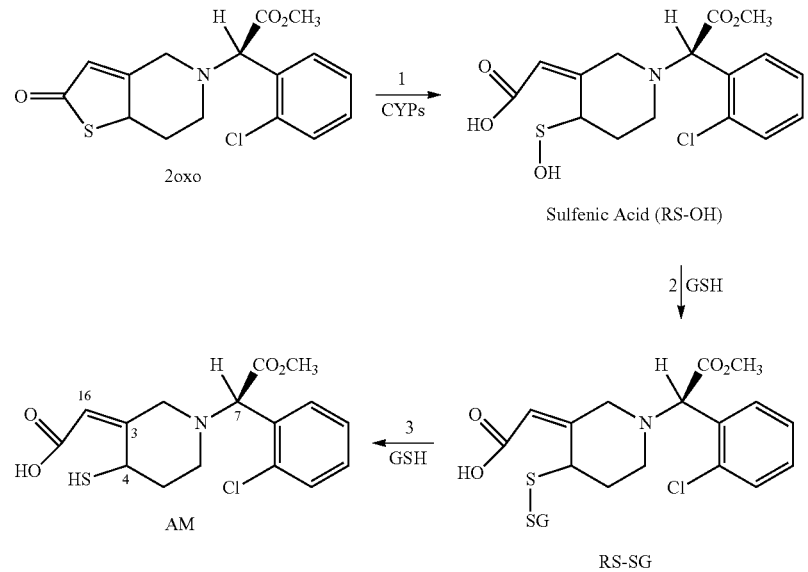

According to Scheme 2, 2-oxoclopidogrel is first oxidized to a sulfenic acid intermediate by P450s. The highly unstable sulfenic acid is then rapidly reduced by glutathione (GSH) to form a mixed disulfide conjugate (RS-SG) that is subsequently reduced by another GSH molecule to form the AM. This is consistent with the observation that GSH is required for the formation of the AM in human liver microsomes (HLMs) (see, e.g., Kazui M, et al., (2010) Drug Metab Dispos 38(1):92-99). It is widely accepted that the AM is responsible for inhibition of platelet aggregation through covalent modification of platelet $P2Y_{12}$ receptor (see, e.g., Ding Z, et al., (2003) Blood 101(10):3908-3914; Algaier I, et al., (2008) J Thromb Haemost 6(11):1908-1914). The anti-platelet activity of the mixed disulfide conjugate RS-SG remains untested.

Metabolism of 2-oxoclopidogrel in the presence of N-acetyl-L-cysteine (NAC) and L-cysteine leads to the formation of both the AM and mixed disulfide conjugates (see, e.g., Zhang H, Lau W C and Hollenberg P F (2012) Mol Pharmacol 82:302-309). In addition, it was demonstrated that the mixed disulfide conjugates of NAC and L-cysteine exchange thiols with GSH and that the equilibrium between the AM, the AM conjugate and GSH is governed by their redox potentials. The redox potential of the sulfenic acid intermediate is likely to be high because it is a reactive oxidant.

To overcome drawbacks associated with thienopyridine compounds, mixed disulfide conjugates of thienopyridine compounds were developed. It is contemplated that the mixed disulfide conjugates of thienopyridine compounds of the present invention are capable of producing active metabolites in the presence of endogenous glutathione (GSH) without the need for bioactivation by P450s, as illustrated in Scheme 3. It is contemplated that this approach will not only bypasses the oxidative bioactivation process by P450s, but will circumvent many of the drawbacks of the thienopyridinyl drugs. For example, it is contemplated that jugates is predictable. In addition, it is contemplated that use of the mixed disulfide conjugates of thienopyridine compounds of the present invention as antiplatelet agents will reduce the toxicity because toxic reactive metabolites are not produced by the thiol-exchange reaction. In addition, it is contemplated that the therapeutic onset time for the mixed disulfide conjugates of thienopyridine compounds of the present invention will be shortened, which greatly benefits patients who experience acute cardiovascular events. The standard regimen for thienopyridines requires continuously dosing patients for 3-5 days because only a small percentage of ingested thienopyridines are converted to the active metabolite. In contrast, it is contemplated that the mixed disulfide conjugates of thienopyridine compounds of the present invention can release the active metabolites with high yields in less than 30 min. In addition, it is contemplated that the mixed disulfide conjugates of thienopyridine compounds of the present invention will have superior stability over the active metabolites and therefore they can be used to quantitatively generate the active metabolites for basic and clinical research in vitro.

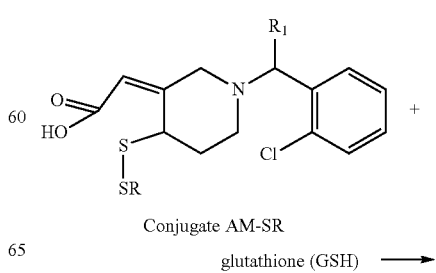

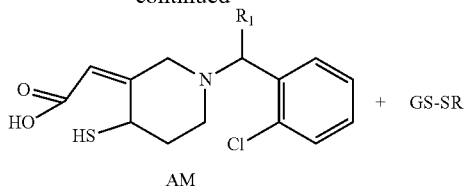

AM

Within Scheme 3, examples of SR include, but are not limited to,

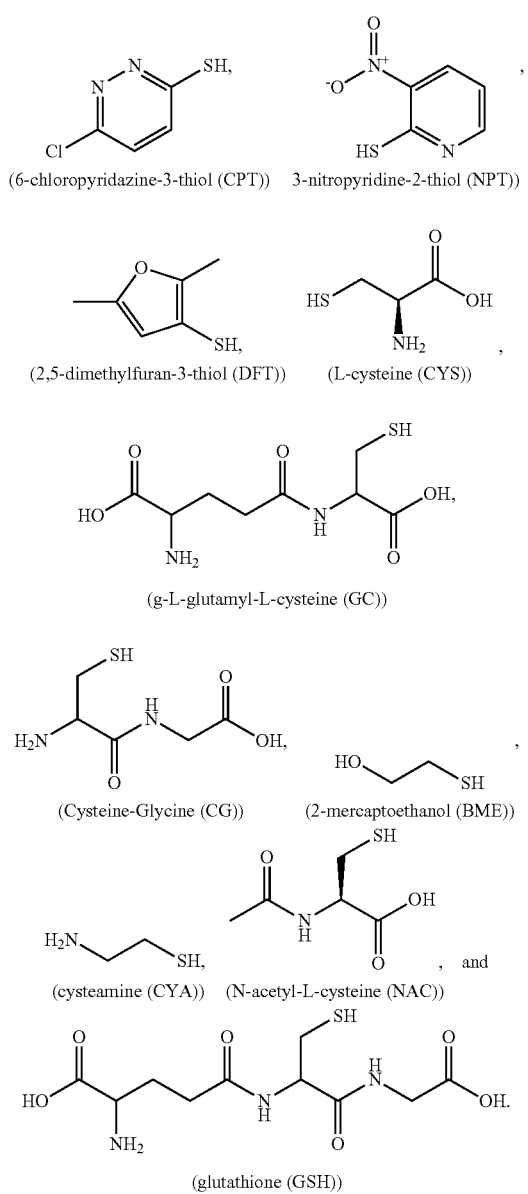

Accordingly, the present invention relates to mixed disulfide conjugates of thienopyridine compounds which are capable of producing active thienopyridine metabolites in the presence of endogenous glutathione (GSH) without the need for bioactivation by P450s. The invention further relates to methods of treating, ameliorating, or preventing cardiovascular disorders in a patient, such as those that are responsive to antiplatelet agents (such as clopidogrel, ticlopidine, and prasugrel) comprising administering to a patient a mixed disulfide conjugate of a thienopyridine compound of the invention. Such disorders include, but are not limited to, coronary artery disease, peripheral vascular disease, and cerebrovascular disease. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used within pharmaceutical compositions configured for intravenous (IV) administration (e.g., in medical situations requiring IV administration of antiplate agents (e.g., coronary angioplasty)).

The present invention is not limited to particular mixed disulfide conjugates of thienopyridine compounds. In some embodiments, the mixed disulfide conjugates of thienopyridine compounds are described by Formula I:

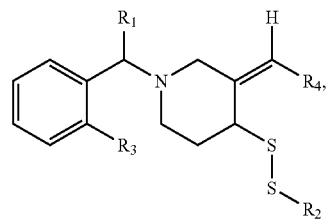

including pharmaceutically acceptable salts, solvates, and/or prodrugs thereof, wherein R4 is selected from the group consisting of an ester moiety with an aliphatic and/or aromatic substituent, a ketone moiety with an aliphatic and/or aromatic substituent, and an amide moiety with an aliphatic and/or aromatic substituent.

Formula I is not limited to a particular chemical moiety R1, R2, R3, and R4. In some embodiments, R1, R2, R3, and R4 each independently include any chemical moiety that renders the resulting compound capable of producing active thienopyridine metabolites upon interaction with endogenous glutathione (GSH) (e.g., active thienopyridine metabolites capable of antiplatelet activity). In some embodiments R1, R2, R3, and R4 each independently include any chemical moiety that renders the resulting compound capable of producing active thienopyridine metabolites in the presence of endogenous glutathione (GSH) without the need for bioactivation by P450s. In some embodiments, R1, R2, R3, and R4 each independently include any chemical moiety that renders the resulting compound capable of treating, ameliorating, or preventing cardiovascular disorders (e.g., coronary artery disease, peripheral vascular disease, and cerebrovascular disease) in a patient, such as those that are responsive to antiplatelet agents (such as clopidogrel, ticlopidine, and prasugrel). In some embodiments, R1, R2, R3, and R4 each independently include any chemical moiety that renders the resulting compound capable of inhibiting platelet aggregation by, for example, altering the function of platelet membranes by blocking ADP receptors (e.g., thereby preventing a conformational change of glycoprotein IIb/IIIa which allows platelet binding to fibrinogen). In some embodiments, R1, R2, R3, and R4 each independently include any chemical moiety that renders the resulting compound capable of reducing aggregation ("clumping") of platelets by irreversibly binding to P2Y$_{12}$ receptors.

Such mixed disulfide conjugates are not limited to particular stereochemical configurations within Formula I

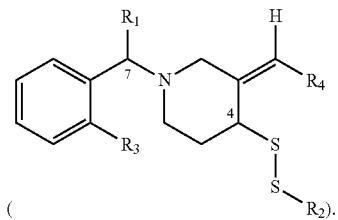

In some embodiments, the double bond connected with the R4 substituent is either in a Z or cis configuration. For example, in some embodiments, Formula I is represented by any of the following stereochemical configurations:

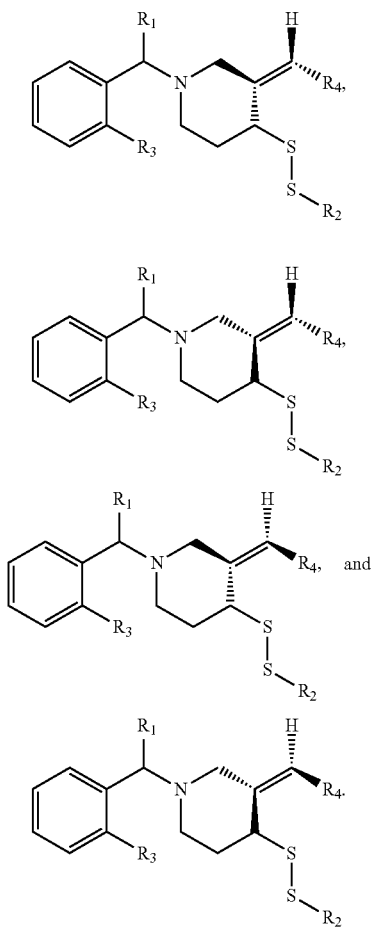

In some embodiments, the C7 carbon is either in a racemic, R or S configuration. For example, in some embodiments, Formula I is represented by any of the following stereochemical configurations:

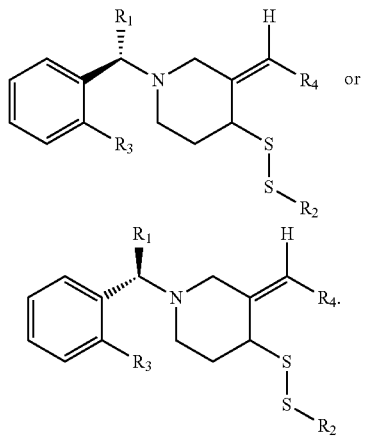

In some embodiments, the C7 carbon is either in a racemic, R or S configuration. For example, in some embodiments, Formula I is represented by any of the following stereochemical configurations:

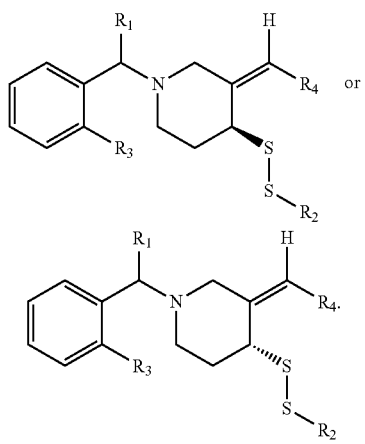

In some embodiments, the compound encompassed within Formula I contains one or more stereochemical configurations for the double bond connected to R4 (e.g., Z or cis configuration), the C7 carbon (e.g., racemic, R or S configuration), and the C4 carbon (e.g., racemic, R or S configuration).

In some embodiments, the compound encompassed within Formula I is in a pharmaceutically acceptable salt form. For example, in some embodiments, the R4 substituent is engaged with an applicable metal to form a salt (e.g., Li, Na, K, etc)

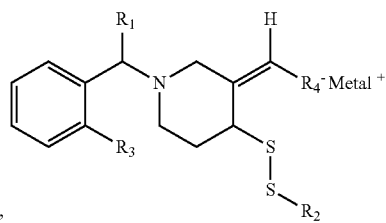

In some embodiment, R1 is selected from the group consisting of H, —CO—OCH3,

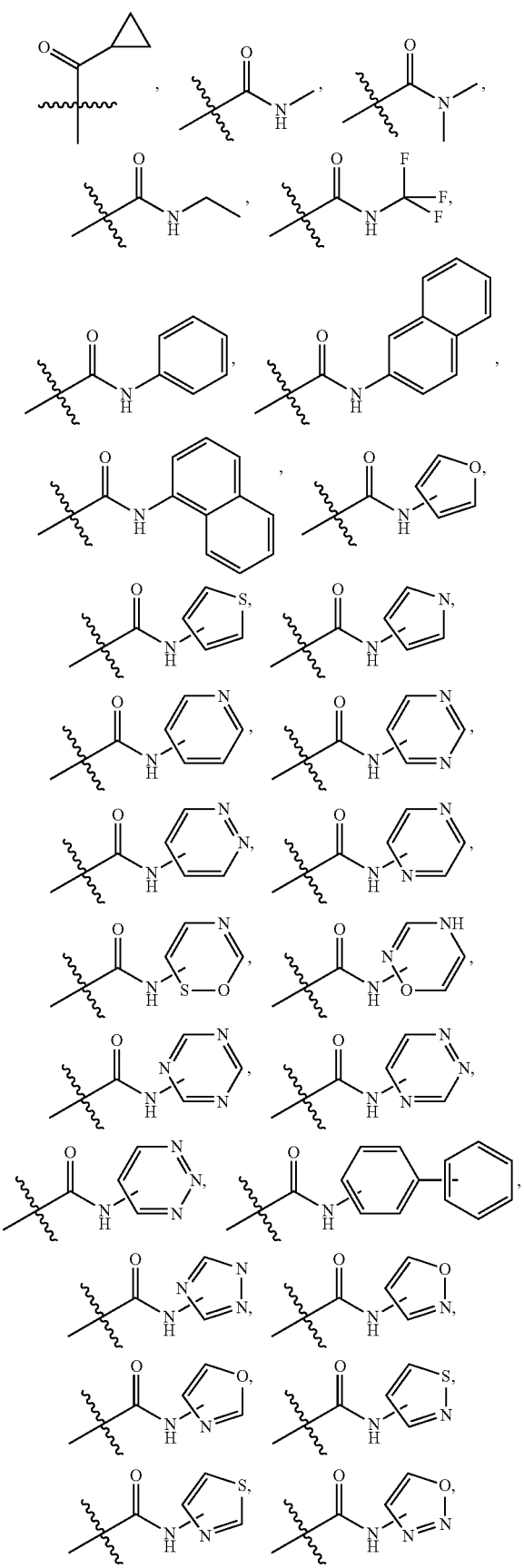

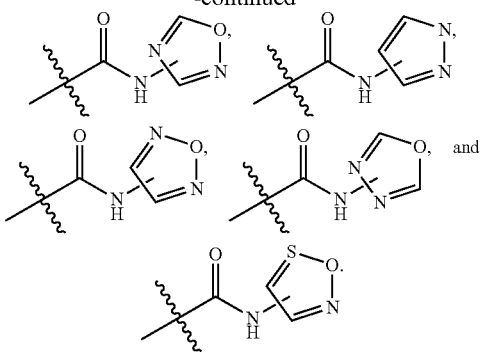

In some embodiments, R2 is selected from the group consisting of

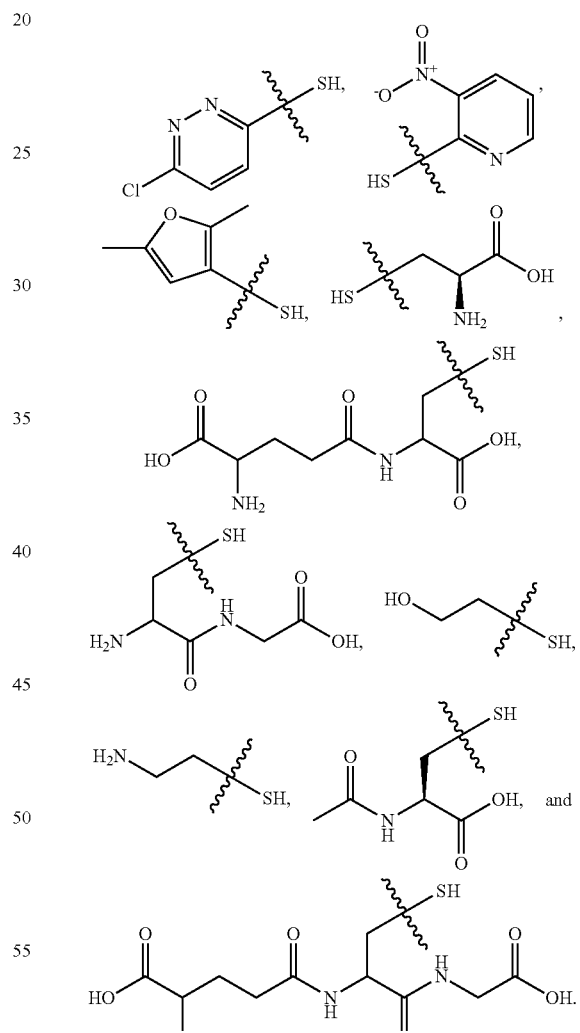

In some embodiments, R3 is an electron withdrawing group. In some embodiments, R3 is a halogen. In some embodiments, R3 is selected from Cl, Br, I, F, CN, NO$_2$, CF$_3$, H, OCH$_3$. In some embodiments, R3 is selected from a halogenated hydrocarbon group such as a trifluoromethyl group; a carboxyl group; an alkoxycarbonyl group such as a methoxycarbonyl group; an aryloxycarbonyl group such as a phenoxycarbonyl group; abn acyl group such as an acetyl group; an acyloxy groups such as an acetoxy group; a cyano group; an aryl group; a 1-alkenyl group; a nitro group; a sulfo group; an alkanesulfonyl group; an alkanesulfinyl group; and an alkoxysulfonyl group.
In some embodiments, R4 is any form of a salt.
In some embodiments, R4 is selected from —COOCH3, —COOCH2CH3, COOCF3,
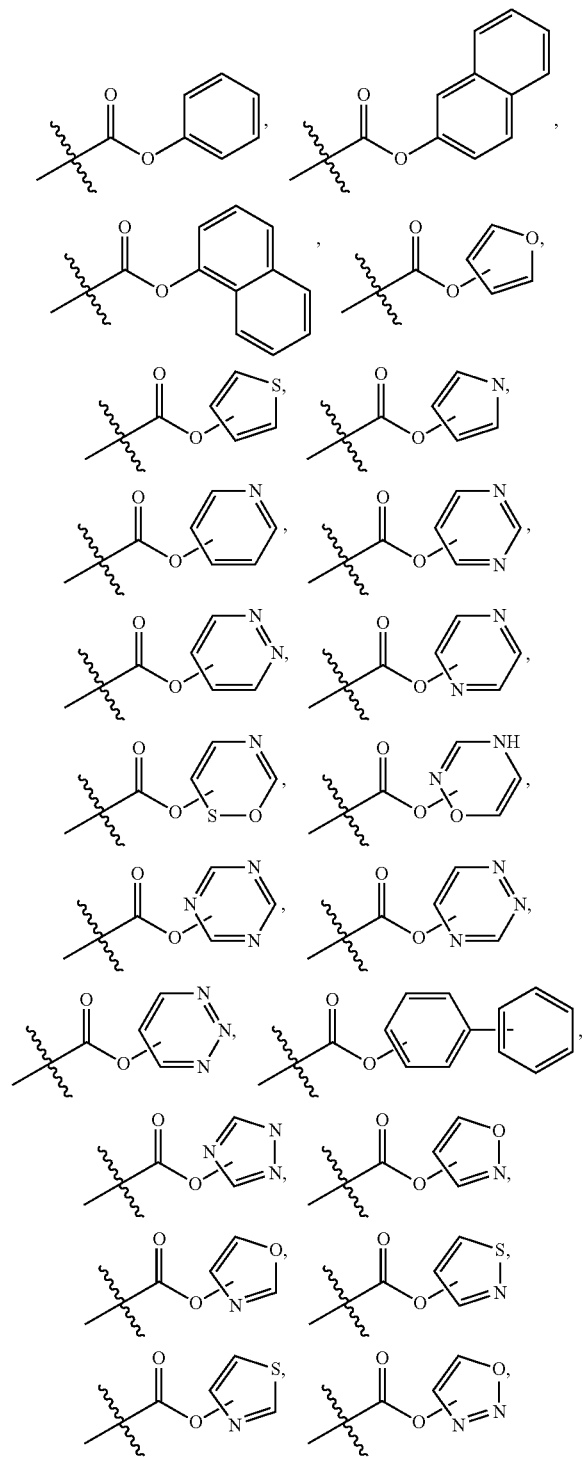
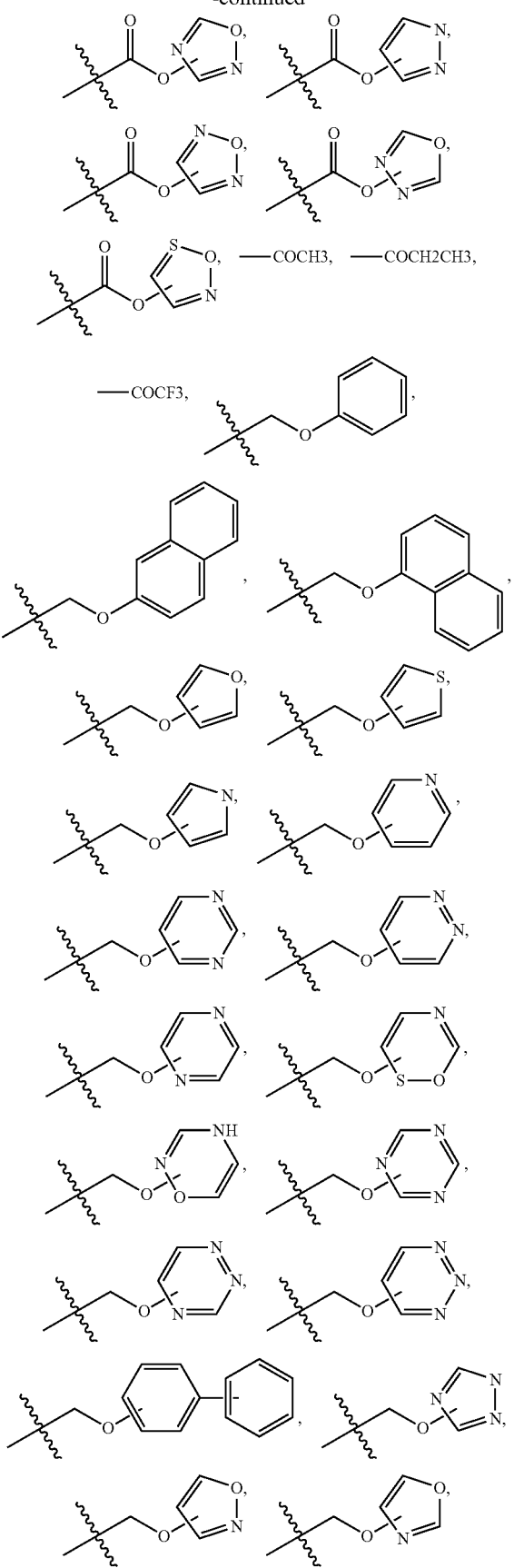

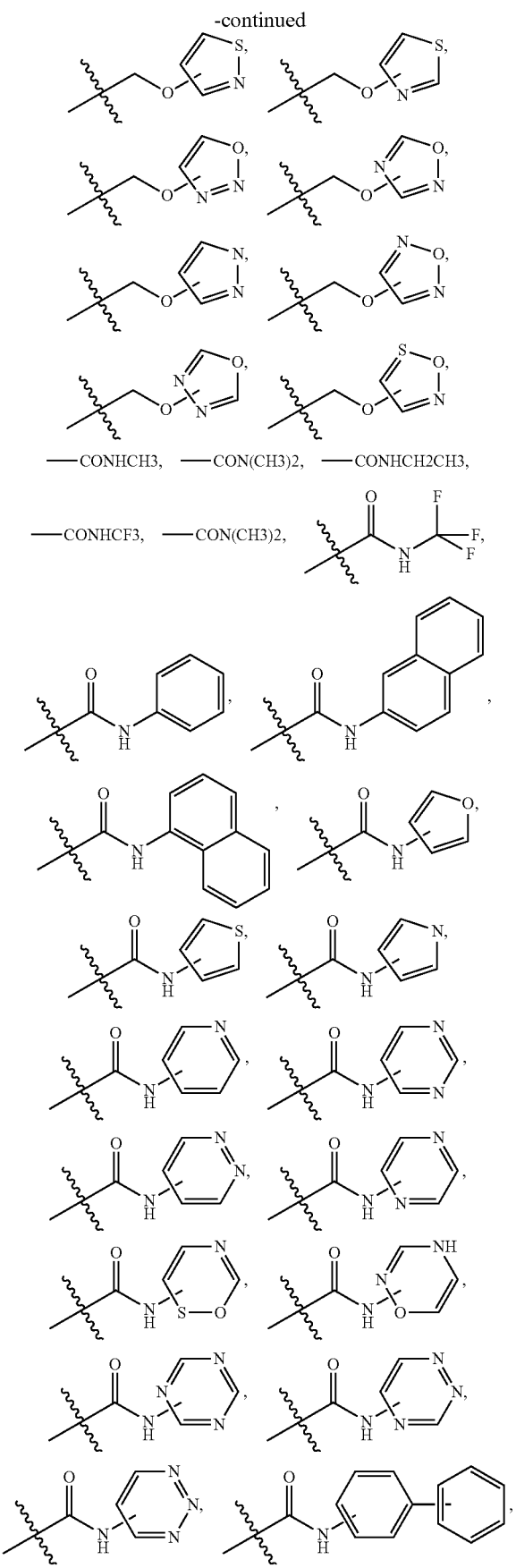

In some embodiments, the compounds are conjugated with a targeting moiety. For example, in some embodiments, the compounds are conjugated with an agent for targeting tumor cells. In some embodiments, the compounds are conjugated with antibodies that target tumor cells.

In some embodiments, the mixed disulfide conjugates of thienopyridine compounds are used to treat, ameliorate, or prevent cardiovascular disorders in an animal (e.g., a mammalian patient including, but not limited to, humans and veterinary animals), such as those that are responsive to antiplatelet agents (such as clopidogrel, ticlopidine, and prasugrel) comprising administering to a patient a mixed disulfide conjugate of thienopyridine compound of the invention. Such disorders include, but are not limited to, coronary artery disease, peripheral vascular disease, atherothrombosis, and cerebrovascular disease. Indeed, in some embodiments, the mixed disulfide conjugates of thienopyridine compounds are used to decrease platelet aggregation and/or inhibit thrombus formation. In this regard, such diseases and pathologies are amenable to treatment or prophylaxis using the present methods and mixed disulfide conjugates of thienopyridine compounds.

In some embodiments, the mixed disulfide conjugates of thienopyridine compounds are used in the prevention of vascular ischemic events in patients with symptomatic artherosclerosis. In some embodiments, the mixed disulfide conjugates of thienopyridine compounds are used to treat or prevent acute coronary syndrome without ST-segment elevation. In some embodiments, the mixed disulfide conjugates of thienopyridine compounds are used for the prevention of thrombosis after placement of intracoronary stent. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used to prolong bleeding time. In some embodiments, the mixed disulfide conjugates of thienopyridine compounds are used to decrease incidence of stroke in high-risk patients.

In some embodiments, the present invention provides pharmaceutical compositions comprising mixed disulfide conjugates of thienopyridine compounds configured for intravenous (IV) administration. In some embodiments, such pharmaceutical compositions comprising mixed disulfide conjugates of thienopyridine compounds configured for intravenous (IV) administration are used in the treatment, amelioration and prevention of atherothrombosis. In some embodiments, such pharmaceutical compositions comprising mixed disulfide conjugates of thienopyridine compounds configured for intravenous (IV) administration are used for rapid inhibition of platelet aggregation. In some embodiments, such pharmaceutical compositions comprising mixed disulfide conjugates of thienopyridine compounds configured for intravenous (IV) administration are used during percutaneous coronary intervention procedures (e.g., coronary angioplasty) for rapid inhibition of platelet aggregation. Indeed, anti-platelet therapy is at the cornerstone of prevention and treatment of atherothrombosis. Platelet activation by agonists such as plaque rupture and sheer pressure stress from stents plays an important role in the development of atherothrombosis. Under certain clinical situations where patients suffer acute cardiovascular syndromes or undergo percutaneous cardiovascular intervention, rapid and complete inhibition of platelet aggregation is needed to prevent cardiovascular deaths and ischemic complications. Such medical scenarios require intravenous administration of anti-platelet agents that possess short onset time. However, this is still an unmet medical need since the anti-platelet agents currently being used either have slow onset time or cannot be administrated intravenously (see, e.g., Silvain, J., and Montalescot, G., (2012) Circ. Cariovasc. Interv. 5:328-331). The mixed disulfide conjugates of thienopyridine compounds of the present invention fulfill this unmet medical need as such compounds can be administrated both orally and intravenously and possess short onset time.

Some embodiments of the present invention provide methods for administering an effective amount of a mixed disulfide conjugate of a thienopyridine compound of the invention and at least one additional therapeutic agent (including, but not limited to, a therapeutic agent known to treat, ameliorate, or prevent cardiovascular disorders), and/or therapeutic technique (e.g., a surgical intervention). A number of therapeutic agents known to treat, ameliorate, or prevent cardiovascular disorders are contemplated for use in the methods of the present invention. Indeed, the present invention contemplates, but is not limited to, administration of numerous therapeutic agents known to treat, ameliorate, or prevent cardiovascular disorders. Examples include, but are not limited to, HMG-CoA reductase inhibitors (e.g., Atorvastatin (Lipitor), Pravastatin (Pravachol) Simvastatin (Zocor), Rosuvastatin (Crestor), Pitavastatin (Livalo), Lovastatin (Mevacor, Altocor), Fluvastatin (Lescol)), ACE Inhibitors (e.g., Ramipril (Altace), Quinapril (Accupril), Captopril (Capoten), Enalapril (Vasotec), Lisinopril (Zestril)), Calcium Channel Blockers (e.g., Amlodipine (Norvasc), Nifedipine (Procardia), Verapamil (Calan), Felodipine (Plendil), Diltiazem (Cardizem)), Platelet Aggregation Inhibitors (other than Ticlopidine, Clopidogrel, and Prasugrel) (e.g., Abciximab (ReoPro), Aspirin, Warfarin (Coumadin), Heparin), Polyunsaturated Fatty Acids (e.g., Omega-3 polyunsaturated fatty acid (Fish Oil)), Fibric Acid Derivatives (e.g., Fenofibrate (Tricor), Gemfibrozil (Lopid)), Bile Acid Sequestrants (e.g., Colestipol (Colestid), Cholestyramine (Questran)), Antioxidants (e.g., Vitamin E), Nicotinic Acid Derivatives (e.g., Niacin (Niaspan), Thromboytic agents (e.g., Alteplase (Activase)), and Antianginal Agents (e.g., Ranolazine (Ranexa).

In some embodiments of the present invention, a mixed disulfide conjugate of thienopyridine compound of the invention and one or more additional therapeutic agent is administered to an patient under one or more of the following conditions: at different periodicities, at different durations, at different concentrations, by different administration routes, etc. In some embodiments, the mixed disulfide conjugate of thienopyridine compound is administered prior to the additional therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the additional therapeutic agent. In some embodiments, the mixed disulfide conjugate of thienopyridine compound is administered after the additional therapeutic agent, e.g., 0.5, 1, 2, 3, 4, 5, 10, 12, or 18 hours, 1, 2, 3, 4, 5, or 6 days, or 1, 2, 3, or 4 weeks after the administration of the additional therapeutic agent. In some embodiments, the mixed disulfide conjugate of thienopyridine compound compound and the additional therapeutic agent are administered concurrently but on different schedules, e.g., the mixed disulfide conjugate of thienopyridine compound is administered daily while the additional therapeutic agent is administered once a week, once every two weeks, once every three weeks, or once every four weeks. In other embodiments, the mixed disulfide conjugate of thienopyridine compound is administered once a week while the additional therapeutic agent is administered daily, once a week, once every two weeks, once every three weeks, or once every four weeks.

Compositions within the scope of this invention include all compositions wherein the mixed disulfide conjugates of thienopyridine compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the mixed disulfide conjugate of thienopyridine compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the mixed disulfide conjugate of thienopyridine compound compound is present at a concentration of about 0.07-1.0 mg/ml, for example, about 0.1-0.5 mg/ml, and in one embodiment, about 0.4 mg/ml.

In addition to administering the mixed disulfide conjugate of thienopyridine compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the mixed disulfide conjugates of thienopyridine compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound having Formula I:

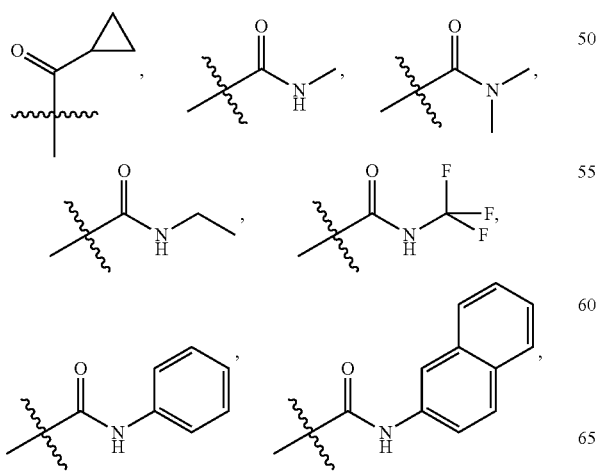

or a pharmaceutically acceptable salt thereof; wherein independently each of $R_1$, $R_2$, $R_3$ and $R_4$ are
$R_1$ is selected from the group consisting of —CO—OCH3,

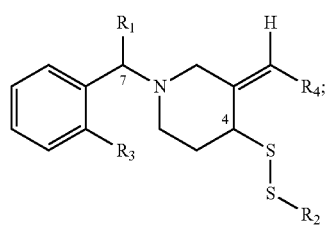

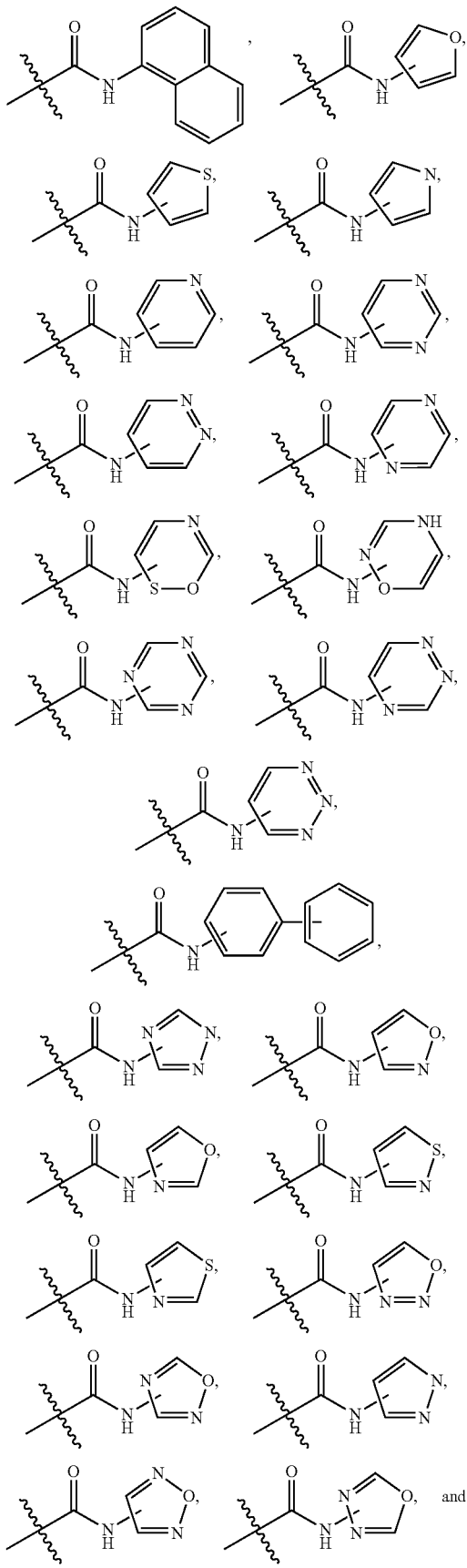

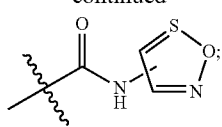
R₂ is selected from the group consisting of
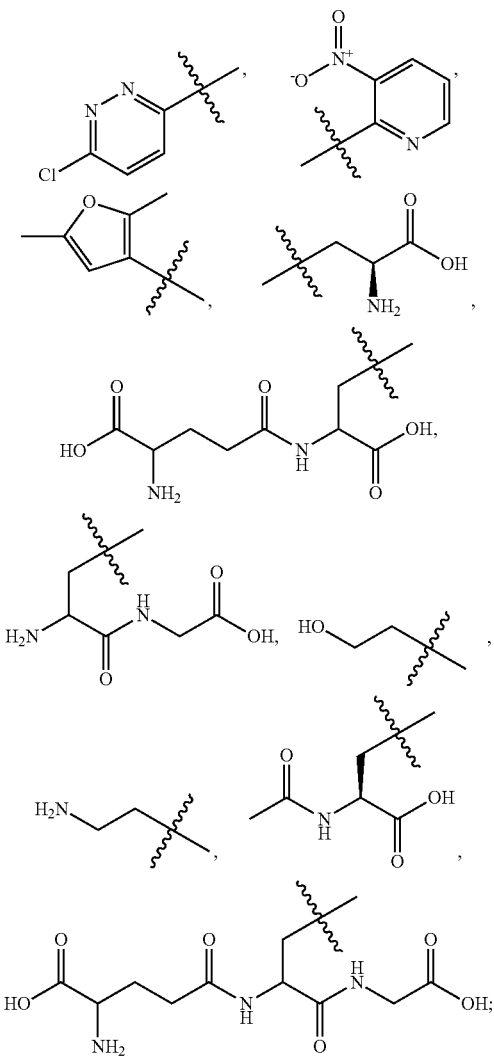
R₃ is selected from the group consisting of Cl, Br, I, F, CN, NO₂, CF₃, H, and OCH₃; and
R₄ is selected from the group consisting of —COOCH3, —COOCH2CH3, COOCF3,
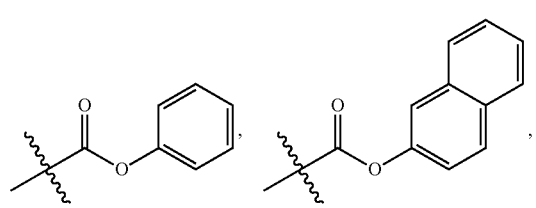
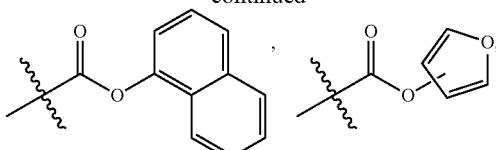
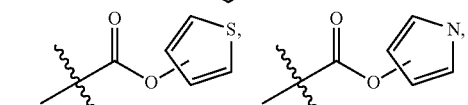
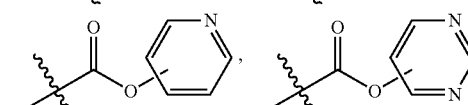
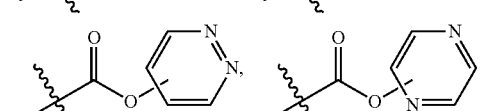
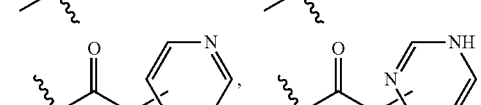
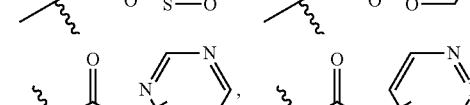
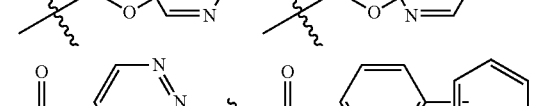
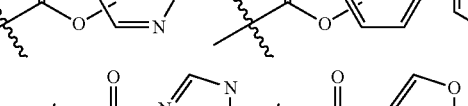
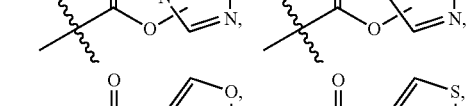
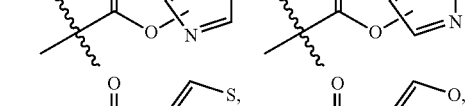
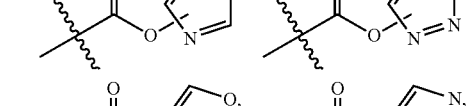
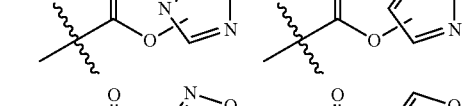
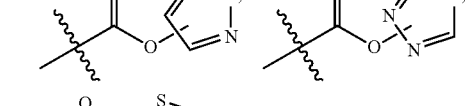
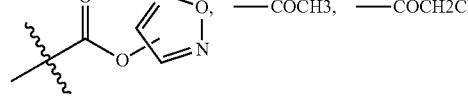
—COCH3, —COCH2CH3,
—COCF3,

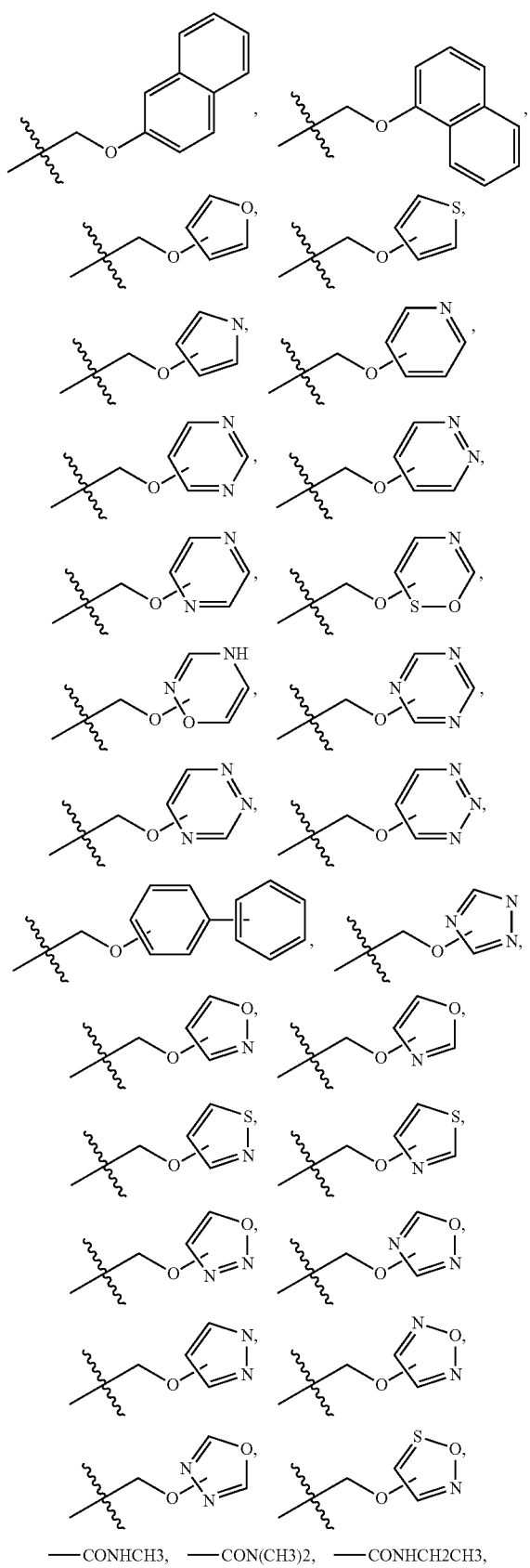
—CONHCH3, —CON(CH3)2, —CONHCH2CH3,
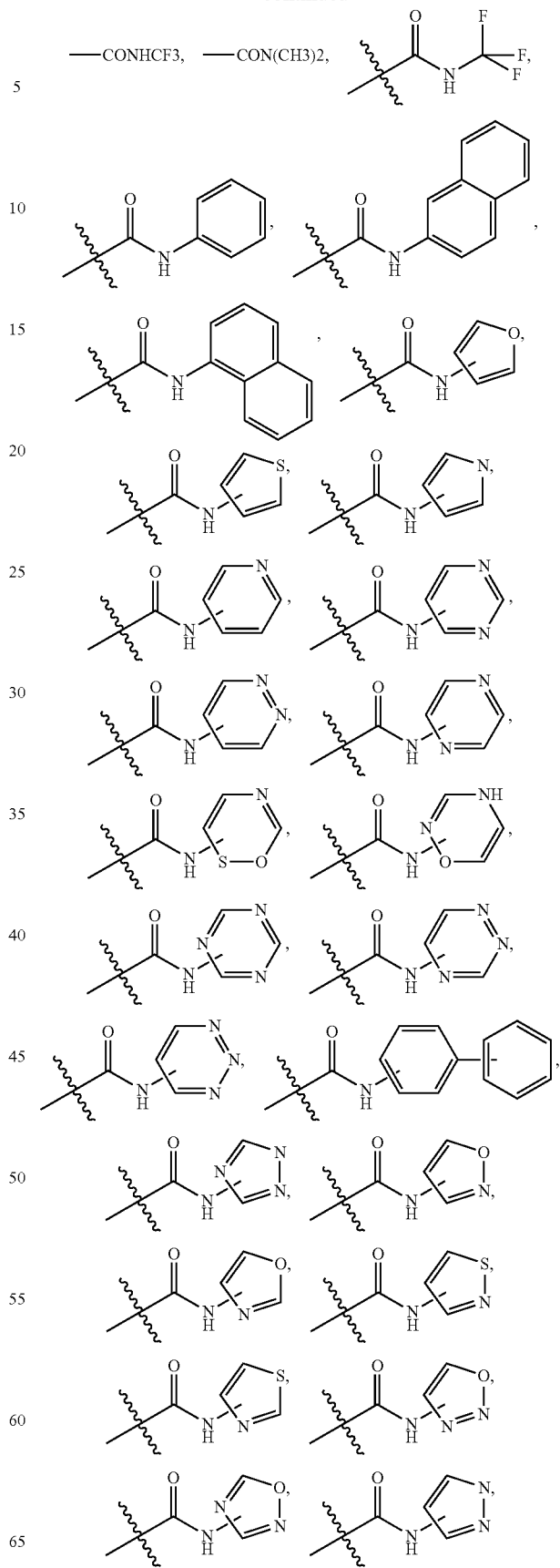
—CONHCF3, —CON(CH3)2,

-continued

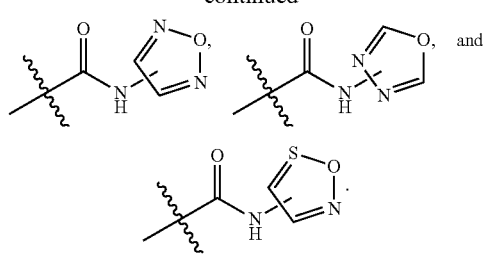

2. The compound of claim 1, wherein stereochemical configuration for Formula I is selected from the group consisting of:

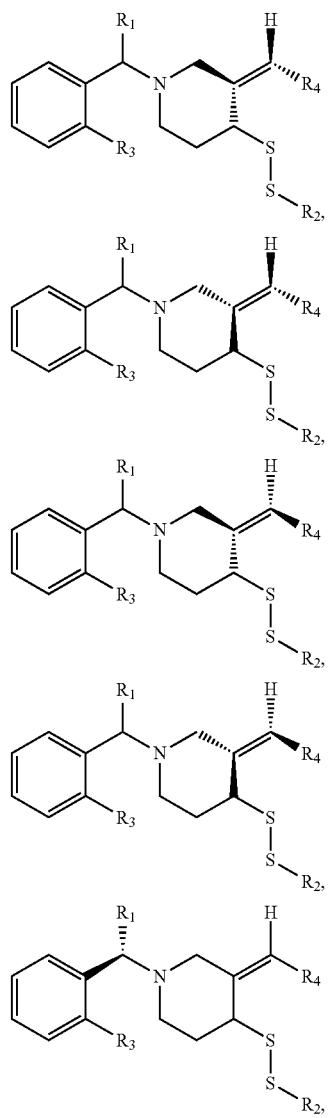

-continued

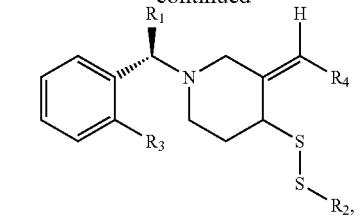

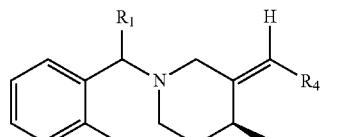

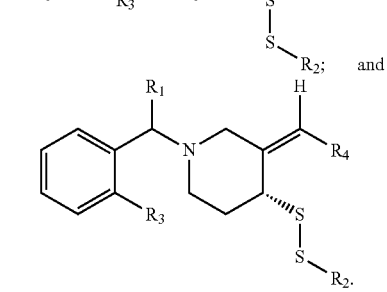

3. The compound of claim 1, wherein the $R_4$ substituent is engaged with an applicable metal to form a salt, wherein the applicable metal is selected from $Na^+$, $K^+$, and $Li^+$, or wherein the $R_4$ substituent is engaged with an applicable halogen to form an ammonium salt.

4. A pharmaceutical composition comprising an effective amount of the compound of claim 1, and a pharmaceutically acceptable carrier.

5. A method of treating a cardiovascular disease in a patient comprising administering to said patient a therapeutically effective amount of the compound of claim 1, wherein said administration is selected from the group consisting of oral administration and intravenous administration, wherein said cardiovascular disease is selected from the group consisting of coronary artery disease, peripheral vascular disease, atherothrombosis, and cerebrovascular disease.

6. The method of claim 5, further comprising co-administration of at least one agent selected from the group consisting of a HMG-CoA reductase inhibitor, an ACE inhibitor, a calcium channel blocker, a platelet aggregation inhibitor, a polyunsaturated fatty acid, fibric acid derivative, a bile acid sequestrant, an antioxidant, a thrombolytic agent, and an antianginal agent.

7. The pharmaceutical composition of claim 4, wherein said pharmaceutical composition is configured for intravenous administration.

8. The pharmaceutical composition of claim 7, wherein said pharmaceutical composition is intravenously administered to a patient during a percutaneous coronary intervention procedure.

9. The pharmaceutical composition of claim 8, wherein said percutaneous coronary intervention procedure is coronary angioplasty.

* * * * *